(12) United States Patent
Bradley et al.

(10) Patent No.: US 9,355,307 B2
(45) Date of Patent: May 31, 2016

(54) METHOD AND APPARATUS FOR REAL TIME PERFORMANCE ASSESSMENT

(71) Applicant: GMAX TECHNOLOGY LTD., Cambridge (GB)

(72) Inventors: William James Bradley, Cambridgeshire (GB); Michael Roger Cane, Cambridgeshire (GB); Dominique M. Freeman, La Honda, CA (US)

(73) Assignee: GMAX TECHNOLOGY LTD., Cambridge (GB)

( * ) Notice: Subject to any disclaimer, the term of this patent is extended or adjusted under 35 U.S.C. 154(b) by 0 days.

(21) Appl. No.: 14/469,848

(22) Filed: Aug. 27, 2014

(65) Prior Publication Data

US 2014/0364980 A1 Dec. 11, 2014

Related U.S. Application Data

(63) Continuation of application No. 12/301,047, filed as application No. PCT/GB2007/001809 on May 16, 2007, now Pat. No. 8,823,524.

(60) Provisional application No. 60/800,783, filed on May 16, 2006.

(51) Int. Cl.
*A63F 9/24* (2006.01)
*A63F 13/00* (2014.01)
*G06F 17/00* (2006.01)
(Continued)

(52) U.S. Cl.
CPC .......... *G06K 9/00342* (2013.01); *A01K 11/008* (2013.01); *A01K 29/00* (2013.01); *A01K 29/005* (2013.01); *A61B 5/002* (2013.01); *A61B 5/0022* (2013.01); *A61B 5/11* (2013.01)

(58) Field of Classification Search
USPC .......................... 463/1, 20, 22, 25, 39; 700/91
See application file for complete search history.

(56) References Cited

U.S. PATENT DOCUMENTS 3,543,724 A 12/1970 Kirkpatrick et al.
4,540,001 A 9/1985 Ewing
(Continued)

FOREIGN PATENT DOCUMENTS

WO 0108417 A1 2/2001
WO 2004084624 A1 10/2004
(Continued)

OTHER PUBLICATIONS

Kobayashi etal, Application of V200 values for evaluation of training effects in the young Thoroughbred under field conditions, Equine Exercise Physiology 5, Equine vet.J., Suppl 30 (1999) 159-162, Japan.
(Continued)

*Primary Examiner* — Adetokumbo O Torimiro
(74) *Attorney, Agent, or Firm* — Tucker Ellis LLP

(57) ABSTRACT

An apparatus for monitoring performance comprises two elements: a first element (4) for attaching to a human or animal, containing two or more of physiological, biochemical, kinematic, and/or environmental sensors and a processing means which records in memory signals or derivates of signals from said sensors and contains a means of re-transmitting this data to a second element, and a second element (13, 16) containing a display (12, 17) or audio output to present the processed live or previous recorded data to the user.

8 Claims, 13 Drawing Sheets

(51) Int. Cl.
  *G06F 19/00* (2011.01)
  *G06K 9/00* (2006.01)
  *A01K 11/00* (2006.01)
  *A01K 29/00* (2006.01)
  *A61B 5/00* (2006.01)
  *A61B 5/11* (2006.01)

(56) References Cited

U.S. PATENT DOCUMENTS 5,818,354 A  10/1998  Gentry
7,467,603 B2  12/2008  Davies
2002/0010390 A1  1/2002  Guice et al.
2004/0061606 A1  4/2004  Gronvold
2006/0000420 A1  1/2006  Davies
2006/0258914 A1  11/2006  Derchak et al.

FOREIGN PATENT DOCUMENTS

WO  2005004999 A1  1/2005
WO  2006119345 A2  11/2006

OTHER PUBLICATIONS

Lucchedsi-Palli, International Search Report, PCT/GB2007/001809, Oct. 11, 20007, EPO.

METHOD AND APPARATUS FOR REAL TIME PERFORMANCE ASSESSMENT

RELATED APPLICATIONS

This application is a continuation and claims the benefit of priority under 35 U.S.C. §120 of co-pending U.S. patent application Ser. No. 12/301,047, filed Nov. 3, 2009, entitled "Method and Apparatus for Real Time Performance Assessment", which is a national stage application, filed under 35 U.S.C. §371, of PCT Application No. PCT/GB2007/001809, filed May 16, 2007, entitled "Method and Apparatus for Real Time Performance Assessment", which claims priority from U.S. Provisional Patent Application Ser. No. 60/800,783, filed May 16, 2006, entitled "Method and Apparatus for Real Time Performance Assessment", the contents of which are hereby incorporated in their entirety.

BACKGROUND

Monitoring equine fitness is important when both training and competing to ensure that training is efficient without prejudicing animal health and welfare whilst aiming for maximal performance. The more information that can be acquired about the horse's metabolic and physiological status during a given workout, the better the assessment of performance, such that data driven decisions can be made to optimize training An important aim of training is to stimulate the animal's physiology to adapt to a higher level of exertion, thus improving performance. Different equine sports require different optimizations, for example some events favor endurance (predominantly slow twitch muscles, aerobic exercise) and some favor sprint performance (predominantly fast twitch muscles, and anaerobic exercise) such as thoroughbred racing or show jumping. Training aims to stress aspects of the horse's physiology so that fatigue and the resulting compensation lead to adaptation and improved performance over the medium term.

Research has shown that different levels of exercise intensity stress different aspects of the horse's physiology and metabolism. These levels depend both on the natural ability of the animal and it's current level of fitness. These levels can be determined by the measurement of a number of indicators including analysis of blood chemistry, or more conveniently by measurement of heart rate relative to the individual's maximum heart rate. This measurement is useful in determining a desired level of exercise during training to achieve the continued improvement as the horse's fitness progresses. The ability of the horse to recover after exercise is also a measure of fitness. This can be determined by monitoring changes in heart rate over time relative to the horse's maximum and resting heart rates. Additionally the ability of the muscles to tolerate high levels of lactic acid has been used as an index of performance. Blood lactic acid level has been correlated to heart rates to indicate when exercise is in the aerobic or anaerobic zones.

Over training can lead to injury including dehydration, metabolic distress and damage to bone, ligament, tendon and cartilage, some of which is irreversible. It is therefore important to choose a training regime that stresses the relevant aspect of the animal's physiology, maximizing that stress consistent with the level of fitness of the animal and to do this without causing injury or distress. Providing a complete picture of the horses metabolic and physiologic state with kinetic (speed, acceleration, distance, elevation) data and ambient conditions in combination with feed, farrier, radiological, immunization and therapeutic regimens will result in the most complete data set on which to derive training profiles and assess performance output for individual horses.

Current practice relies on the experience of the trainer and in some cases 'static' physiological measurements taken before and after training, and on trackside measurements of speed. These measurements include body temperature, weight, heart rate, respiration rate and in some cases blood chemistry. Performance improvement is most often measured by timing the horse over a standard course.

Recently, equine heart rate monitors (manufactured by Polar, Garmin and others) have been introduced and are used during training or competition allowing a 'dynamic' or continuous monitoring of heart rate during exercise. These systems can provide a read out of heart rate and speed when combined with a built in GPS system. Data may be displayed to the rider via a wrist or arm mounted display unit. These devices can be programmed to trigger alerts based on reaching certain heart rates. These systems may log data for download after use to a PC. The trainer then uses software supplied with the monitor to compare performance against previous training sessions to assess changes in performance.

This data can be combined with observations of behavior, feeding, body weight or condition, gait, body temperature and respiratory rate to assess the health of the animal, to regulate feeding, and to establish if training should proceed, or be altered or discontinued.

Kobayashi (Equine Vet J Suppl 1999 July 30:159-62) showed that by standardizing training regimes, heart rate and speed monitoring can provide a quantitative assessment of the effect of training by calculating the theoretical velocity the horse can achieve with a heart rate of 200 bpm (V200). This is achieved by measuring heart rate at a range of speeds and by using linear regression to calculate the theoretical speed at a heart rate of 200 bpm. V200 was shown to increase with fitness. The difficulty with implementation of this method in day to day training is that heart rate and speed measurements must be acquired and V200 calculated manually for each horse, which is a time consuming and skilled task prone to error in a day to day training environment.

WO2004/084624 describes a device in the saddle blanket that monitors equine heart rate and velocity and can transmit this information to a trainer's PC via a radio data link. This allows a trainer to monitor a number of horses during training and automate the calculation of V200. The disadvantage however is that this apparatus requires hard wired connections between the blanket, girth and rider that are inconvenient in operation for example if the rider were to fall, and during mounting and dismounting.

U.S. Pat. No. 4,540,001 describes a heart rate monitor integrated into a girth. This apparatus does not include speed sensing so is limited in its ability to monitor heart rate only.

These inventions do not solve the problem of combining physiological, biochemical, environmental and kinetic information into one device which is obtained during training for on the fly and or retrospective analysis of performance and performance improvement.

What is needed is a device for performance assessment and training, most particularly for use when training a horse. Embodiments of the invention are directed to a device affixed to a horse to monitor the horse during exercise using a combination physiological, biochemical, environmental and kinematic sensors to acquire process and display the performance metrics and type of exercise regime to be performed by the horse based upon a predetermined exercise programme.

SUMMARY OF THE INVENTION

In one embodiment the apparatus affixed to the horse monitors the physiological and biochemical status of a horse by incorporating one or more physiological biosensors and a processing means. The apparatus may be affixed to the horse using the girth, the saddle, saddle blanket or pad, harness, breastcollar or other tack, protective gear or horse clothing. The apparatus may transmit the signal from the sensors wirelessly using a proprietary communications protocol, or though standard communications protocols such as Bluetooth, to a display unit. This display unit may be worn by a rider or trainer, or may be affixed to the saddle, bridle or harness. The display unit may also be a may be a laptop, PC, PDA or cellular phone. The data may be saved in a database for retrospective comparison along with similar data acquired in training regimes, and may be used to set the training regimes. Data such as age, sex, weight, ID, vaccination, farrier record, track or course conditions, radiological or therapeutic intervention can be entered. There may be two way communications between the display unit and the rider or trainer for changing the training regime during the workout. Multiple horses may be trained simultaneously each with said device affixed to each horse where the data is offloaded to a central display device for data storage, post processing assessment and training adjustment and advice. In addition the method of acquiring the data, processing the data and communicating the results in an automated fashion is disclosed. Integration of sensors with data processing in a single attachment to the horse is novel.

In another embodiment the sensors may be directly implanted in the animal. Examples include implanted glucose or other implantable or minimally invasive biosensors, physiological sensors such as temperature sensors, airway humidity sensors for determining cardiac output or other sensors such as those for measuring blood flow or A-VO2 differences. Implanted identification devices such as RFID chips which can transmit identity and or location of an animal can be included. Signals from these implanted or minimally invasive physiological, biological and radiofrequency sensors are combined in a central processing means, and the data acquired used for optimizing performance in training and competition or in tracking or monitoring wildlife including but not limited to birds, fish, game and endangered or migratory species.

BRIEF DESCRIPTION OF THE DRAWINGS

The invention will now be further described, by way of example, with reference to the accompanying drawings, in which.

DETAILED DESCRIPTION

Figure 1:
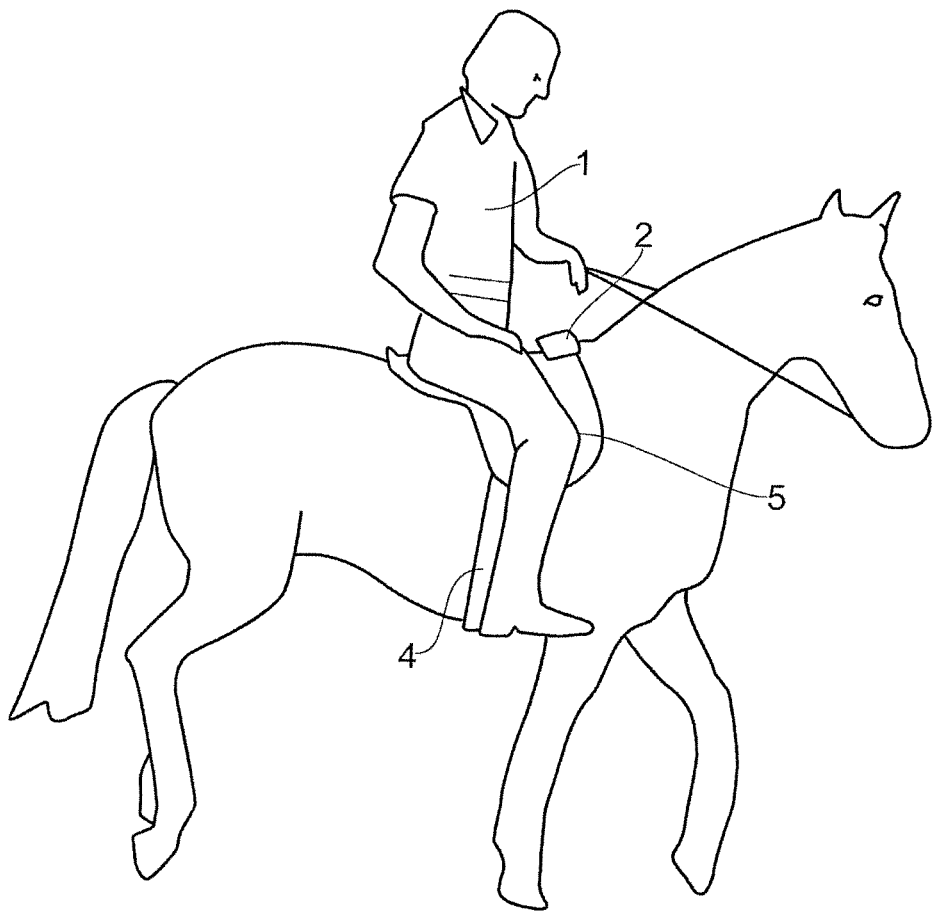
FIG. 1 is a side view of the horse and rider showing the arrangement of the 'active girth' and 'display unit' in a form attached saddle"
Figure 2:
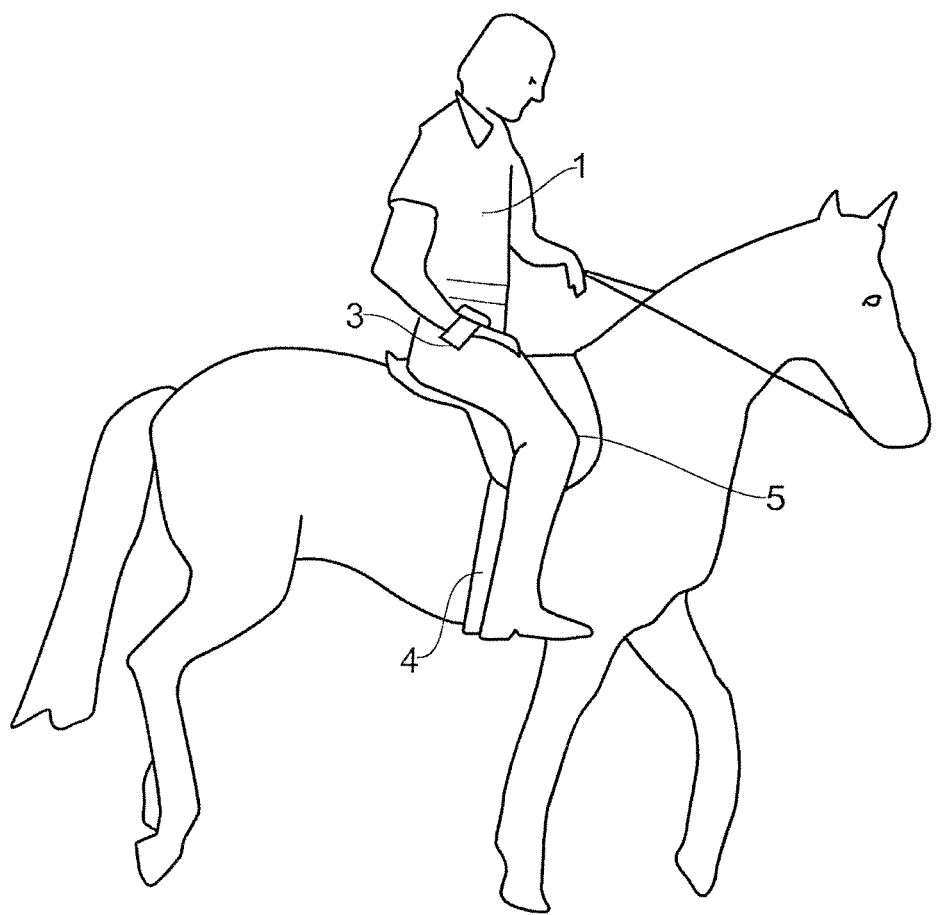
FIG. 2 is a side view of the horse and rider showing the arrangement of the first element or 'active girth' and second element or 'display unit' in a form worn by the rider.

It is the object of this invention to combine in a convenient manner all physiological, biochemical, ambient, gait, speed, distance and location parameters into a single system for performance assessment in humans or animals, in particular equines.

In a first embodiment the invention provides an apparatus for use when training a horse, the apparatus comprising a first element and second element. The first element attaches to a horse and includes physiological, biochemical, environmental or kinetic sensors. The sensors in use, generate signals indicative of the metabolic condition of a horse. The first element further comprises a processing means.

The second element of the apparatus comprises a display for displaying the type of exercise to be performed, which, in use, generates a training signal based upon the signals received from the sensors and a predetermined training programme, the training signal being indicative of the type of exercise that the horse should perform at that time.

In a second embodiment of element one the sensors may be implanted in the horse and communicate wirelessly with the first element which contains a processing means.

Embodiments of the apparatus preferably monitor the health state of a horse and the apparatus may therefore include the following features in a self-contained first element comprising of two or more sensors and processing means to monitor the sensors and derive data from them.

The first element may include (but is not limited to) one or more of the following sensors:

An accelerometer [0039] A heart rate sensor. [0040] A skin temperature sensor [0041] A blood glucose or lactate sensor [0042] A position sensor (altitude, speed, distance) [0043] A breath sensor [0044] Environmental sensors such as humidity and ambient temperature [0045] A radiofrequency ID chip reader In a preferred embodiment the first element may be (but not limited to) a girth, or a tubular cover or sleeve, which fits over a girth, or may be affixed to or embedded in a saddle. The first element may have a means of transmitting and receiving derived data with the second element to provide a data link. The data link may transmit data which has been processed by the processing means to reduce the quantity of data. The first element preferably has sufficient memory to log and store data from sensors/inputs. The first element may include a means of transmitting and receiving data with an external PC or data network.

The second element may have a visual display and be embodied in a format that can be worn by the rider or alternatively embodied in a format that can be attached to the saddle, the tack, or embedded in the saddle, or is a remote device such as a laptop, computer, cell phone or PDA.

The second element may be optional; its primary purpose is to provide live visualisation of sensor signals measured by the first element or to indicate a signal to direct the training It may also be used as a means of configuring the first element. The second element may have a means of transmitting and receiving derived data with the first element. The second element may have at least one electrical button which can be operated by the rider. This button could be in the form of a touch screen, joystick or other method. The first or second element may include a means of reading electronic identification tags which are commonly implanted in horses to identify them. The second element may include a means of transmitting and receiving data with an external PC. The second element may be wrist mounted and may include a real time display of physiological parameters and velocity and gradient.

Further wired and wireless elements may be added to the system for additional functionality. For example, the first element may communicate with a user's PDA or mobile phone. The first or second element may be configurable with a code chip, or wireless identity card or RFID card.

The apparatus preferably includes a one or more processors which, in use, run algorithms that process the data and make predictive outcomes. The system preferably compares current performance with records of previous performance or a predefined performance target.

Further advantages of the invention are realized when more than one horse is under training as it simplifies the management of training programmes and facilitates the analysis of performance of individual horses in a training group.

An example of the apparatus for monitoring the health status of a horse will now be described with reference to FIGS. 1 to 12.

In one embodiment the apparatus consists of two elements; the 'active girth' 5 and a display unit either worn by the rider 3 or mounted to the saddle 2.

The active girth combines a girth with sensors and an integrated electronic system to process, store and transmit the data received from the sensors. The active girth is self-contained so that there is no additional equipment to be fitted to the horse compared with conventional tack, and no wires have to be connected which can be time consuming. Positioning of the sensors is reproducible and robust, reducing variation in signal or poor signal quality due to operator error. The preferred embodiment includes a heart rate sensor that detects electrical signals from the horse using two conductive pads 9 & 11, which are in contact with the horse's skin when the girth is fitted. It also contains a temperature sensor 10 that is held in contact with the horse's skin and a 3-axis solid-state accelerometer 18. It also contains environmental sensors 22, including ambient temperature and relative humidity sensor. It also contains a positioning system, in this case a GPS receiver 21, alternatives may include a terrestrial based radio triangulation system. Thus a particular benefit of the invention is that by combining a number of sensors into a single apparatus the calculation of performance indicators that are not possible from one sensor alone is now conveniently achieved. These performance indicators include, but are not limited to: [0055] V200 and VHRMax can be calculated from the heart rate and speed (derived from the position sensor) [0056] Gait frequency can be obtained from analysis of accelerometer data. When accelerometer data is combined with speed data, the stride length can be calculated. This is important in assessing work efficiency, fitness and for the detection of gait abnormalities as would be associated with lameness. [0057] Heat stress can be derived from ambient temperature and relative humidity and is a critical index of how the environment may effect performance, and thus more informative than either of these measurements taken individually [0058] Energy expenditure or calories consumed using measurements of heart rate, speed and gait pattern (e.g. trotting, walking etc) and body temperature may be used to derive a measurement of energy expended by the animal which can be used to guide feeding and training such as glycogen loading protocols.

Figure 5A:
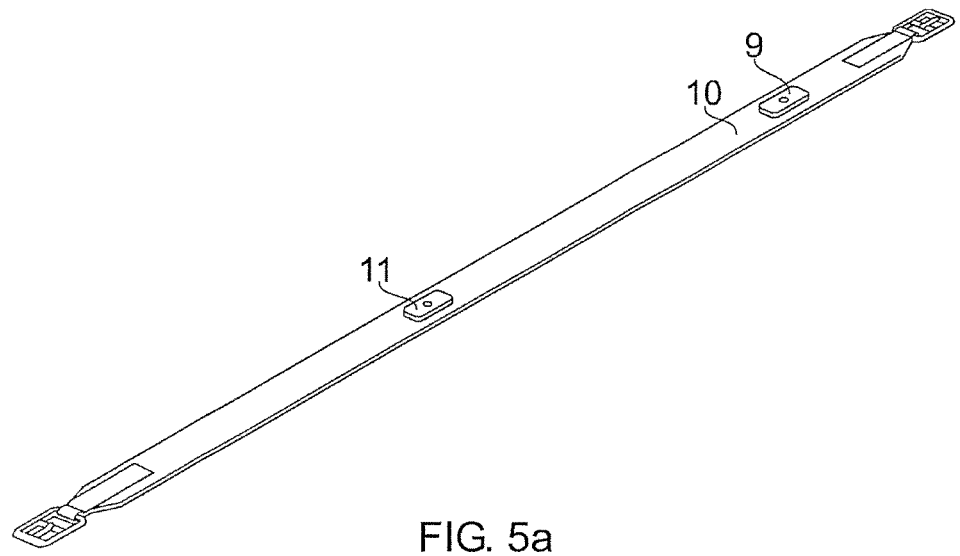
FIG. 5(a) shows top side of the first element or 'active girth'.
Figure 5B:
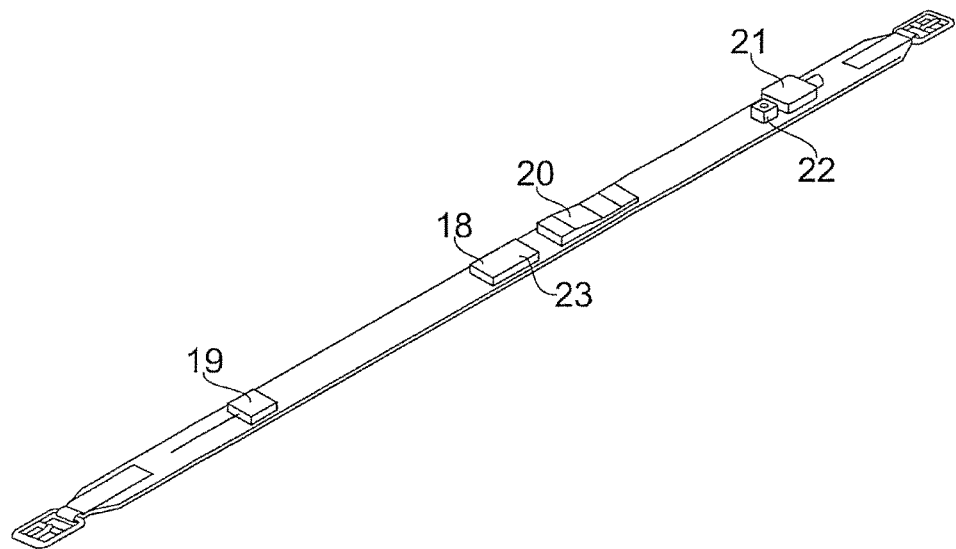
FIG. 5(b) shows the bottom side of the first element or 'active girth'
Figure 5C:
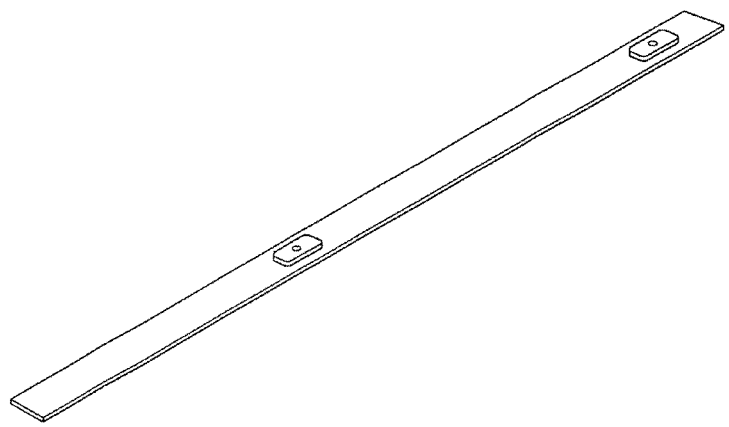
FIG. 5(c) shows the top side of a sleeve incorporating the electronic system which can be fitted over an existing girth, to turn it into an 'active girth'
Figure 5D:
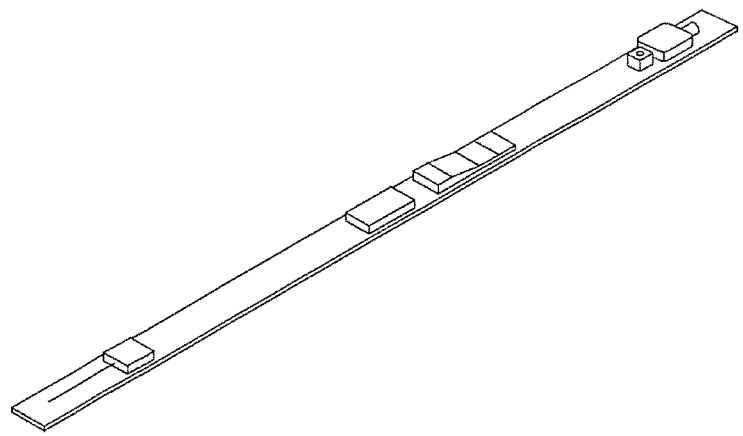
FIG. 5(d) shows the bottom side of a sleeve incorporating the electronic system which can be fitted over an existing girth, to turn it into an 'active girth'
Figure 6:
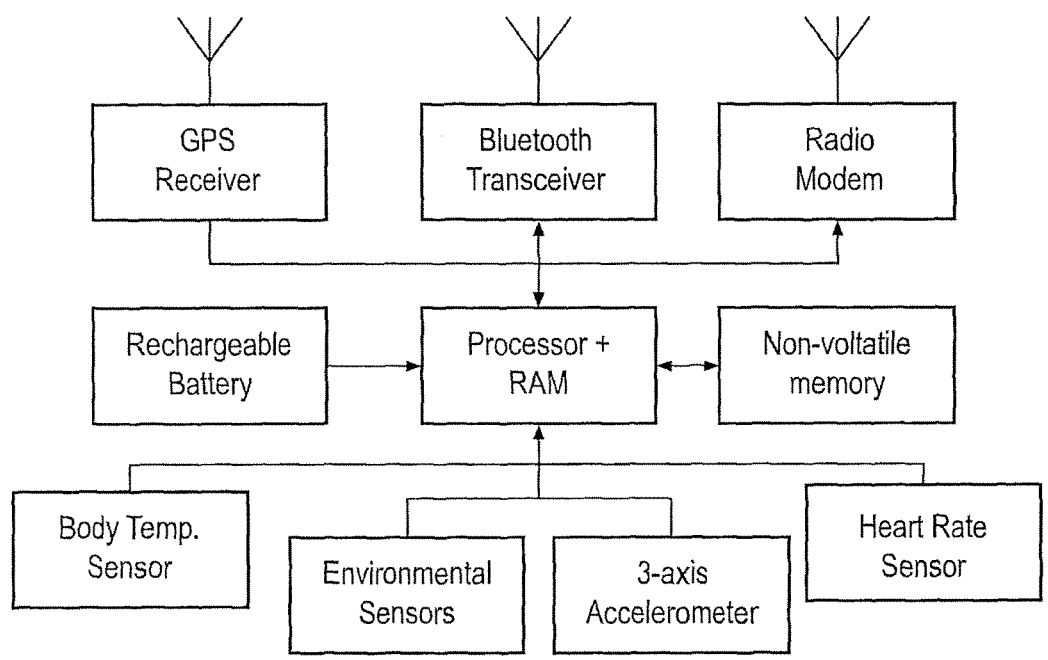
FIG. 6 shows a block diagram of the electronic system incorporated into the 'active girth'.
Figure 7:
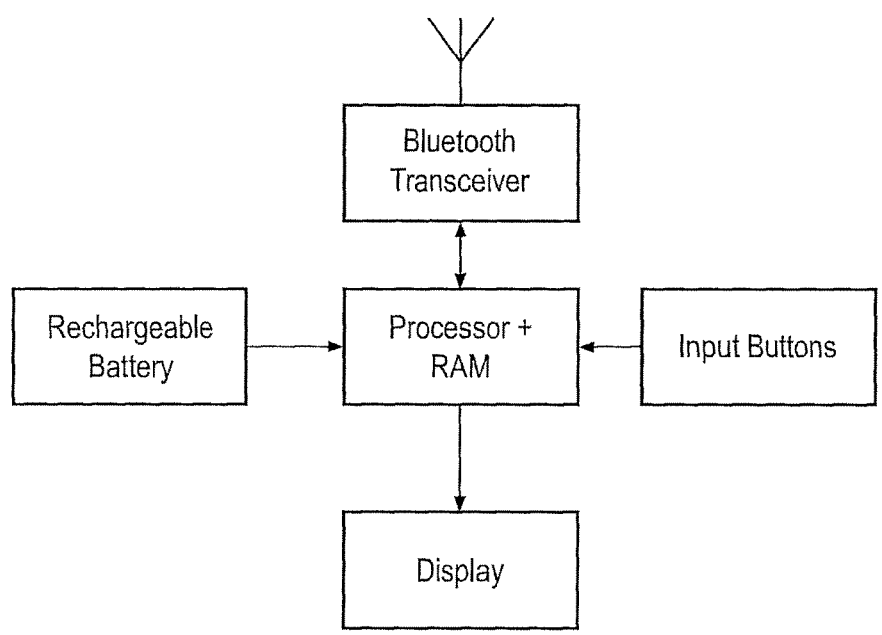
FIG. 7 shows a block diagram of the electronic system incorporated into the display unit.

A block diagram of the electronic system contained in the Active Girth is shown in FIG. 6. The processor reads the sensors and an algorithm may identify relevant features from the data in order to reduce the quantity of data that has to be logged. The data is recorded in memory. In a preferred embodiment the active girth contains the electronics, rechargeable battery and sensors in a rugged and flexible enclosure that forms part of the girth (FIGS. 5c & d). In the preferred embodiment, the battery can be recharged wirelessly using an inductive power transfer system. Alternatively, primary cells or wired recharging can be used. Sealed electrical contacts may be accessible for optional wired charging and communications, in this case using USB.

Figure 11:
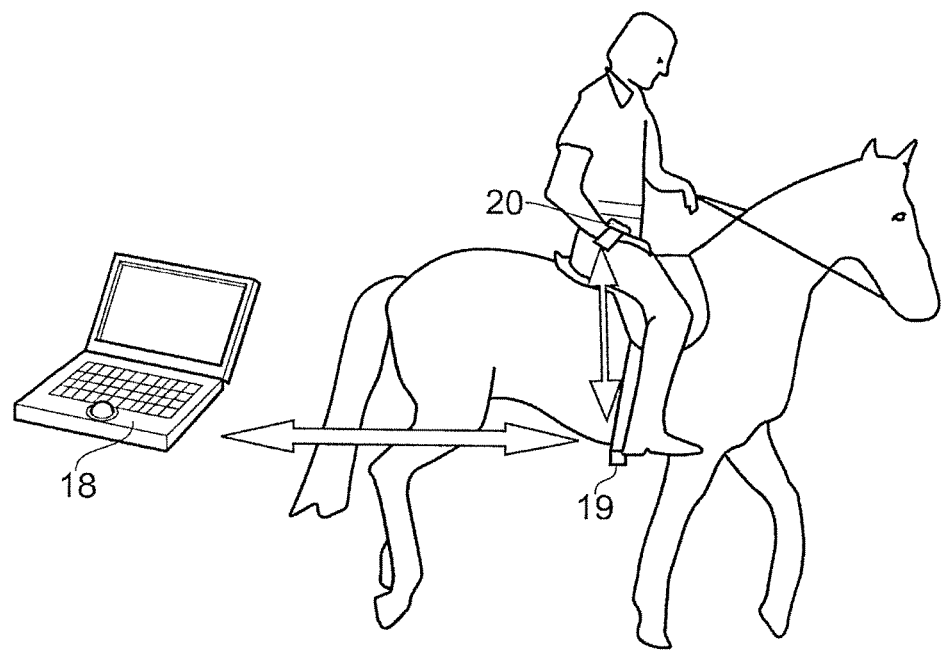
FIG. 11 shows the transfer of data between the elements of the system

The electronic system of the Active Girth also includes a short-range radio telemetry system that is in this case Bluetooth. The main purpose of the short-range telemetry system is to communicate with the display unit, but it may also be used to download data to another external device. FIG. 11 indicates this communication. This communication link downloads data from the display unit's switches to the active girth, and uploads data from the active girth to the display unit. A second longer range radio modem in the active girth may be used to communicate with an external PC. At a minimum this modem requires a range of 10 meters to allow download of data from a moving horse. Ideally the modem would have a range of several kilometers so that the active girth could continuously be in contact with the PC during training Alternatively this modem may utilize a cellular telephone network or other wireless data network (such as wifi). The modem may in fact be part of a cellular telephone, to which the active girth communicates wirelessly (for example with Bluetooth). This network may allow direct access to the Internet or the trainer's PC or both. A secure data communication protocol may be required as a component of the data links used by the system because of the confidential nature of the data being transmitted. The telemetry protocol ensures that paired devices can only communicate with each other even in the presence of other systems on other horses, and it ensures the data transfer is secure. This link allows data from the active girth to be downloaded to the PC, and configuration files and instructions to be uploaded to the active girth.

Figure 4:
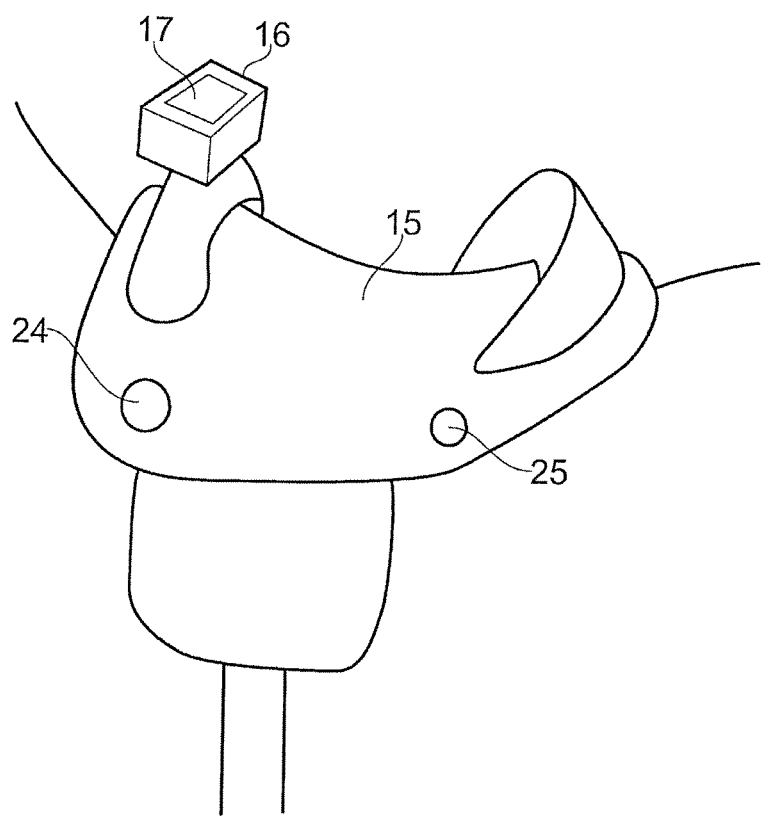
FIG. 4 shows a saddle with the second element or display unit in the form of a unit attached to the pommel, and the first unit attached or embedded directly into the saddle (or "smart saddle";)

In another preferred embodiment the function of the active girth is undertaken by the saddle. Sensors are embedded in the underside of the saddle as shown in FIG. 4 items 24 & 25 as is the short and or long range communication link and processor. Similar embodiments as described for the active girth can be envisioned for other types of horse tack such as bridles, breast collars, harness and horse clothing such as blankets or protective gear such as splint boots, shadow rolls or fly masks.

The software architecture for the system may have several embodiments. In a first embodiment the algorithms that calculate performance metrics from the data recorded from the sensors could reside in the processors in 4 and 3. In this embodiment the system operates independently of the PC. In this embodiment the system may store metrics from previous training sessions for comparison. In a second embodiment the system sends sensor data to the PC for storage and the algorithms operate in software on the PC. These metrics are then sent back to the system. In a third embodiment the system sends the data to a secure server on the Internet for storage and processing of the data. This may be sent directly from the horse based system which acts as the client, or via the PC which acts as the client. The server then returns the calculated metrics to system by a reverse process. In a forth embodiment the system processes the data from the sensors and calculates performance metrics. These metrics are sent either directly or via a PC to the Internet based secure server. The server stores the data and processes it to calculate changes in these metrics over time and present these graphically via user interface. This data could be accessed by trainers and owners over the Internet using a PC with a web browser. A fifth embodiment that combines all of these embodiments is also possible.

Where the long range radio system is installed and permits live monitoring of the horse, it may be used during competition to display live performance data to team members and spectators. Where more than one horse in the same competition is provided with the system, then live comparisons of performance (such as race position or metabolic status) can be provided to the team members, spectators or third party equipment.

Figure 3:
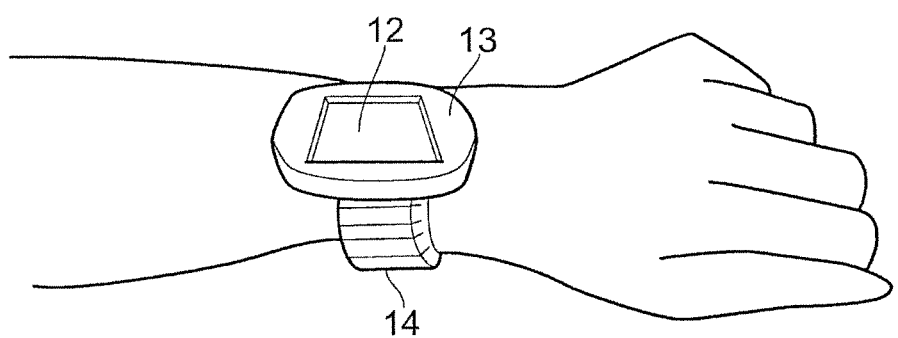
FIG. 3 shows the second element or display unit in the form worn by the rider.
Figure 9:
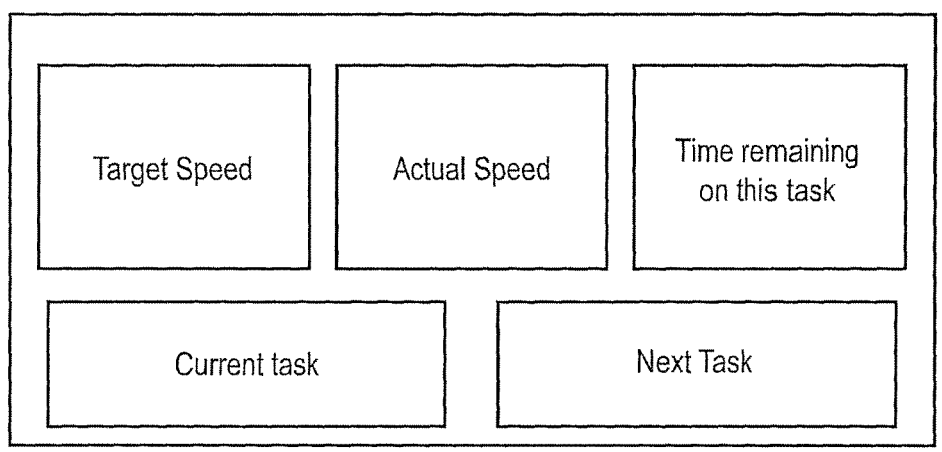
FIG. 9 shows the layout of the display 3.
Figure 10:
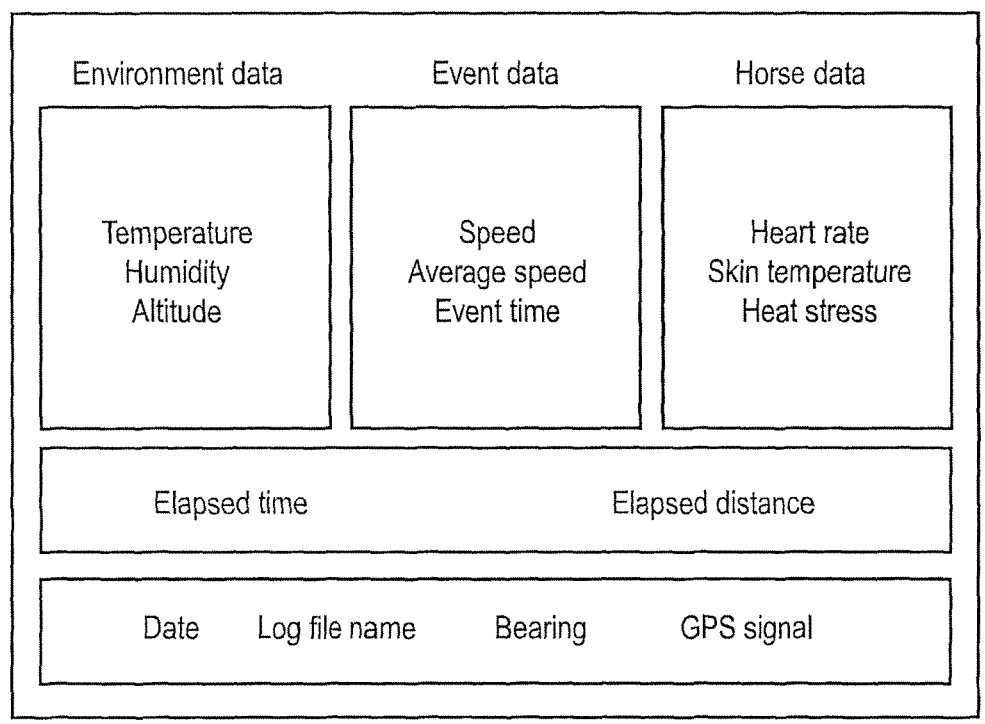
FIG. 10 shows the layout of the display 2.

The display unit has two possible configurations shown in FIG. 3 and FIG. 1, both share the same electronic system shown in FIG. 6. This comprises a wireless transceiver (in this case Bluetooth) which receives data and commands from the active girth or smart saddle. The processor manipulates the data for the display 12 or 17. In the preferred embodiment the screen is an LCD display with a touch screen, but separate buttons surrounding the screen are an alternative. The embodiment shown in FIG. 3 is most suitable for the training of racehorses and an example display layout for this application is shown in FIG. 9. The embodiment shown in FIG. 1 is most suitable for endurance racing and an example display layout for this application is shown in FIG. 10. The purpose of the touch screen or buttons is to allow the rider to indicate the start and end of each new training task or race leg. Feedback from the buttons/touch screen on the display unit may be passed back to the active girth for storage in non-volatile memory with other data, for example, to indicate the start of training The display unit in the case of 1 may be a PDA with customised software. In the case of FIG. 3, the display unit may also function as a wrist-watch with timing functions.

Figure 8:
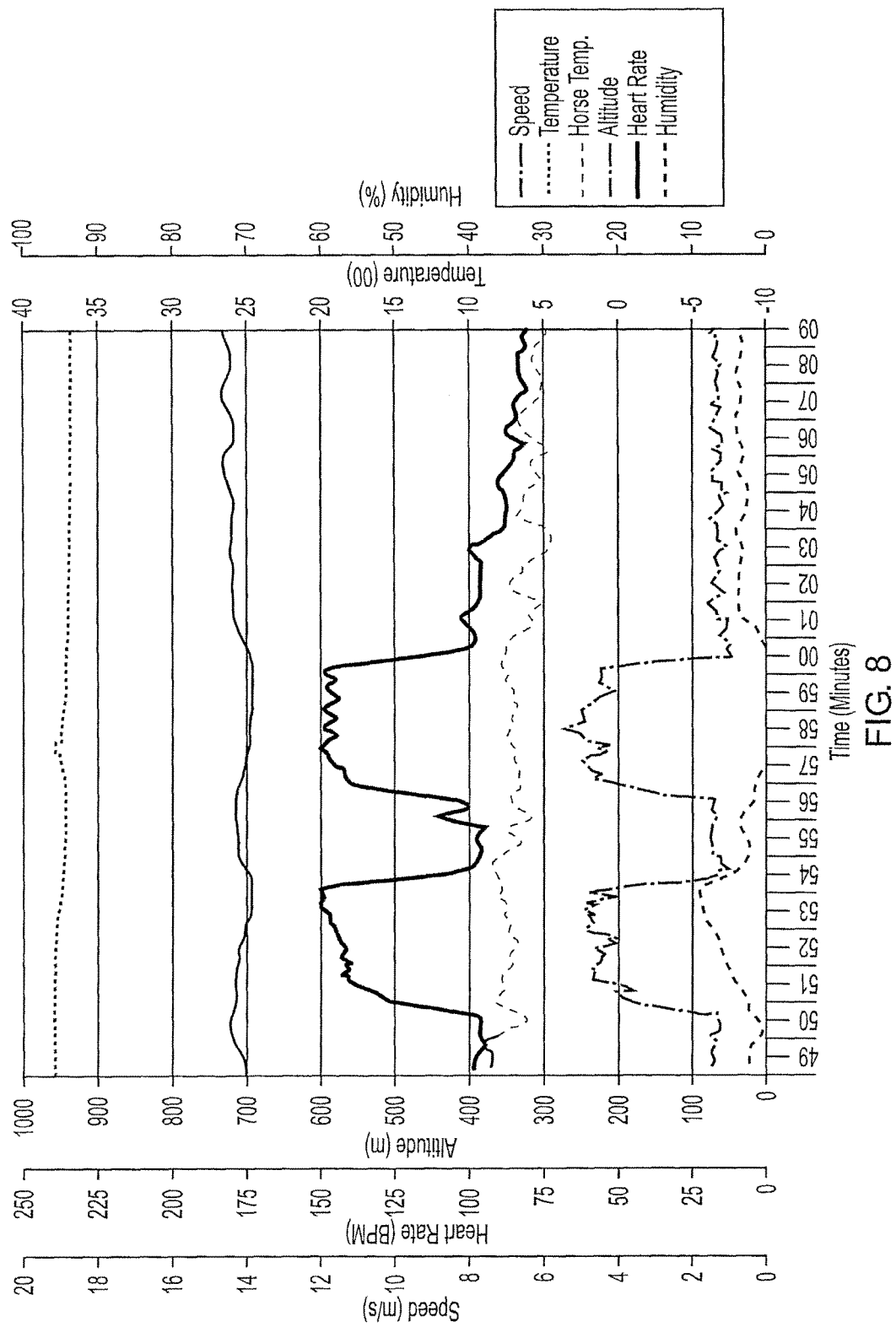
FIG. 8 shows example data recorded from a prototype system.

An example data set received by the PC is shown in FIG. 8.

The operation of one embodiment of the system is described below.

Figure 12:
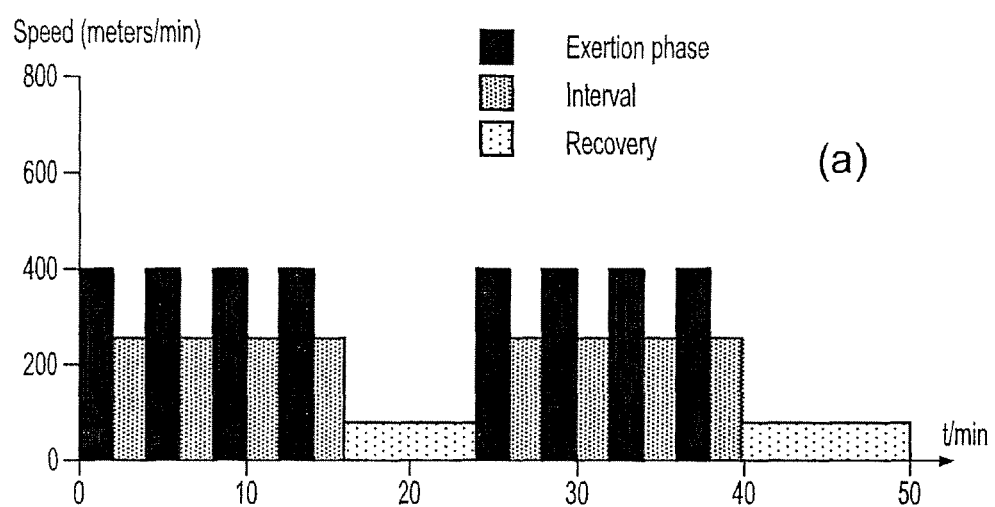
FIG. 12 shows an example training plan

The trainer logs on to the Internet based secure server, selects the horse to be trained and selects from a library of generic training regimes offered on the server depending on the training effect required. The trainer can also define custom regimes. The regime may be suggested by the server software based on statistical analysis of past performance of that horse. FIG. 12 illustrates a typical regime.

When the generic regime is selected the client server software may customise it by referencing horse past performance data and information regarding the training site to be used stored on the server. This data may include V200, HRmax, location, length and gradient of training track. The server software then calculates the target heart rates, horse speeds and repetitions, adds warm up and cool down sequences, and creates a customized training profile specifically for the training session. The data is downloaded via the internet from the client server to a PC located at the stable. As the horse leaves the stable for the training session, the regime is downloaded wirelessly to the processor in the horse based system. Alternatively the training regime can be saved onto a chip which is manually loaded into the processor.

The horse based system then implements the training session and prompts the rider to start the training programme via the display unit. First the software indicates to the rider to start the warm up by requesting sequences of slow speed exercise. This is done by displaying a target speed and actual speed on the display unit for a predetermined time or for so long as the horse is exercising within a predetermined training area, so the rider can aim to match the horse speed to the target speed to provide the proper exercise stress. Execution of these sequences is monitored by the software by reference to the GPS data and other physiological sensors. The training and cool down sequences are then prompted in a similar way. In another embodiment new training sequences can be loaded on the fly to alter training mid stream if performance metrics dictate.

The training plan may also be used as a means of indicating a race strategy to the user, and or an aid to navigating the course. This has particular advantages in endurance competition, in which it is essential for success to correctly pace the horse. In this case, the training plan may be dynamically updated by the device depending on how the course has been ridden so far, or can be adjusted by the support team during the periodic veterinary checks to take into account observations on the horse's welfare.

The software in the horse based system also performs fitness checks during training based on the sensor data. These may include heart rate recovery rate, gait, body temperature, environmental heat stress etc. The rider is warned if normal parameters based on previous training performance or welfare guidelines are exceeded. During the training the sensor data and calculated metrics are logged and uploaded back to the stable PC as the horses return from training This data is then uploaded to the server via the Internet. The data is then added to the database for that horse and the graphical analysis of the horse's fitness over time is updated. The server software allows the trainer or owner to compare current performance against previous sessions with the same regime over the same track. This gives easily understood trends for the trainer to see changes in performance.

In another embodiment groups of horses can be trained remotely using the training regimens which may be started using an electronic "gate". Horse and rider identification can be retrieved through electronic identification as the horses pass through the electronic gate. Simulation of race conditions to measure performance metrics between groups of horses in similar or different training regimes can thus be conveniently obtained and compared for performance outcomes studies. Results can be sent remotely to owners PDA's, cellular telephones, laptop computers or to a website.

A problem with analysing the data provided by the system is that there are many environmental factors that will effect the reaction of the horse to a given training stimulus. To address this problem an improved method of data analysis may include comparison of physiological data with training data just from those training sessions undertaken in similar training conditions. This may include the selection of training data for comparison from data taken from the same training course, duration and intensity as determined by analysis of the position sensing data, and optionally data collected with the same rider, similar weather conditions, ground state or at a similar stage in the season's training programme. This method makes changes in the fitness of the horse more noticeable in the physiological data.

This process may be enhanced further by normalisation of the physiological data using physical and environmental data.

The invention claimed is:

1. A method of monitoring performance of a horse, the method using one or more reference signals derived from an apparatus for monitoring performance, the method comprising providing:
   (a) providing a girth for attaching to a horse, the girth comprising apparatus having two or more of physiological, biochemical, kinematic, and environmental sensors and a processor to record one or more signals from said sensors, wherein the sensors comprise at least an accelerometer sensor and a position sensor;
   (b) attaching the girth to the horse;
   (c) obtaining accelerometer data and position data using said two or more sensors;
   (d) the apparatus having a means of re-transmitting the data to an external device for storage, display or analysis;
   (e) transmitting said data to said external device;
   (f) using said accelerometer data and position data to determine at least a stride length of the horse by combining speed data derived from the position data from the position sensor and accelerometer data derived from the accelerometer sensor;
   wherein said sensors are only in the girth.

2. The method of claim 1, wherein identification chips are worn both by a human and by the horse, the identification chip possessing therein information about the horse selected from at least one of, name, age, weight, gender or patient ID, the identification chip with the human possessing therein information about the human including name and weight and the identification chip with the horse possessing therein information about the horse selected from at least one of, name, age, weight, gender or patient ID, where data acquisition is commenced when the horse or human passes through an electronic gate.

3. The method of claim 1, wherein identification chips are worn both by a human and by the horse, the identification chip possessing therein information about the horse selected from at least one of, name, age, weight, gender or patient ID, the identification chip with the human possessing therein information about the human including name and weight and the identification chip with the horse possessing therein information about the horse selected from at least one of, name, age, weight, gender or patient ID, where an apparatus for monitoring performance is configured when the horse or human passes through an electronic gate which is only large enough for one horse to pass through at a time which reads the identification chips and transmits that data to the said apparatus.

4. The method of claim 1, wherein the sensors comprise a heart rate sensor that detects electrical signals from the horse using conductive pads which are in contact with the horse's skin when the girth is fitted, wherein at least one of the conductive pads is located at a point substantially midway along the length of the girth another of the conductive pads is located near an end of the girth.

5. The method of claim 1, wherein the sensors comprise at least one of:
   a heart rate sensor;
   a skin temperature sensor;
   a blood glucose sensor;
   a lactate sensor;
   a breath sensor;
   a humidity sensor;
   an ambient temperature sensor;
   a radio frequency ID chip reader;
   a code chip to identify the apparatus;
   a wireless identify card;
   an RFID card.

6. A girth for attaching to a horse and for monitoring performance of the horse, the girth comprising:
   two or more of physiological, biochemical, kinematic, and environmental sensors and a processor to record one or more signals from said sensors, wherein the sensors comprise at least an accelerometer sensor and a position sensor, and
   a system configured to determine a least a stride length of the horse by combining speed data derived from position data from the position sensor and accelerometer data derived from the accelerometer sensor;
   wherein said sensors are only in the girth.

7. The girth of claim 6, wherein:
   the girth comprises conductive pads arranged to be in contact with the horse's skin when the girth is fitted;
   the sensors comprise a heart rate sensor configured to use the conductive pads to detect electrical signals from the horse when the girth is fitted,
   wherein at least one of the conductive pads is arranged to be located at a point substantially midway along the length of the girth when the girth is fitted, and another of the conductive pads is arranged to be located near an end of the girth when the girth is fitted.

8. The system of claim 6, wherein the sensors comprise at least one of:
   a heart rate sensor;
   a skin temperature sensor;
   a blood glucose sensor;
   a lactate sensor;
   a breath sensor;
   a humidity sensor;
   an ambient temperature sensor;
   a radio frequency ID chip reader;
   a code chip to identify the apparatus;
   a wireless identify card;
   an RFID card.

* * * * *